US00PP08377P

United States Patent [19]

Spiegel-Roy et al.

[11] Patent Number: Plant 8,377

[45] Date of Patent: Sep. 14, 1993

[54] CITRUS (CITRUS L.) NAMED 'RISHON'

[75] Inventors: Pinchas Spiegel-Roy; Aliza Vardi, both of Ramat Gan; Avraham Elchanati, Holon, all of Israel

[73] Assignee: State of Israel - Ministry of Agriculture, Agricultural Research Organization, Bet Dagan, Israel

[21] Appl. No.: 768,381

[22] Filed: Sep. 20, 1991

[30] Foreign Application Priority Data

May 12, 1991 [IL] Israel ..... 1694

[51] Int. Cl.[5] ..... A01H 5/00

[52] U.S. Cl. ..... Plt./45

[58] Field of Search ..... Plt./45

*Primary Examiner*—James R. Feyrer

*Attorney, Agent, or Firm*—Browdy & Neimark

[57] ABSTRACT

A new variety of mandarin citrus distinguished by very early fruit ripening and fruit which is yellow-orange in color when fully ripe.

1 Drawing Sheet

FIELD OF THE INVENTION

This invention is directed to a novel variety of mandarin tree of the genus Citrus L. which resulted from a controlled pollination made at the Agricultural Research Organization, the Volcani Center, Bet Dagan, Israel between a seed bearing parent Temple and a pollen parent Michal.

BACKGROUND OF THE INVENTION

The objective in breeding the present novel variety, assigned the denomination Rishon, was to obtain an early ripening mandarin citrus wherein the fruit has few seeds.

In the spring of 1978 a controlled pollination cross between Temple (Citrus Temple Hort. ex Y. Tanaka) as a seed bearing parent and Michal (a cultivar of Israeli origin believed to be a natural hybrid between two Citrus Reticulata Blanco cultivars) as a pollen parent was made at the Agricultural Research Organization, the Volcani Center, Bet Dagan, Israel. The fruits were collected in November 1978 and seeds of these fruits were extracted and subsequently germinated during January 1979. About 50 seedlings were grown from these germinated seeds. Each seedling was top grafted on a mature Sour Orange rootstock growing in the Agricultural Research Organization experimental grove, Bet Dagan, Israel.

The first fruits were observed in October–November 1985 and observations of the fruits were again made 1986 and 1987. One of the 50 scions was designated 1/37. This scion was observed to be fully ripe in the last week of September or the first week in October, a period which is very early in the Israel growing season. The fruits of this selection were yellow-orange in color when fully ripe.

Budwood was taken from the above mentioned selection 1/37 and top-grafted in the spring of 1986 on two mature Sour Orange and two Troyer rootstocks growing in an experimental grove of the Agricultural Research Organization, Bet Dagan, Israel. These trees were also numbered 1/37. The first crop of these trees was obtained in 1988. The yield of the scions grafted onto Troyer rootstocks was good. The fruit was fully ripe in the first week of October. The color of the fruit when fully ripe was yellow-orange, and the fruit was easy to peel. The fully ripe fruit had a pleasant flavor, and the juice had a sugar concentration of about 11.0% and an acid concentration of about 1.4%.

SUMMARY OF THE INVENTION

The present invention provides a novel variety of mandarin citrus characterized by very early fruit ripening and fruit which is yellow-orange in color when fully ripe.

BRIEF DESCRIPTION OF THE DRAWINGS

Distinctive characteristics of the new variety are exemplified in the accompanying illustrations in which.

PLANT CHARACTERISTICS

Figure 1:
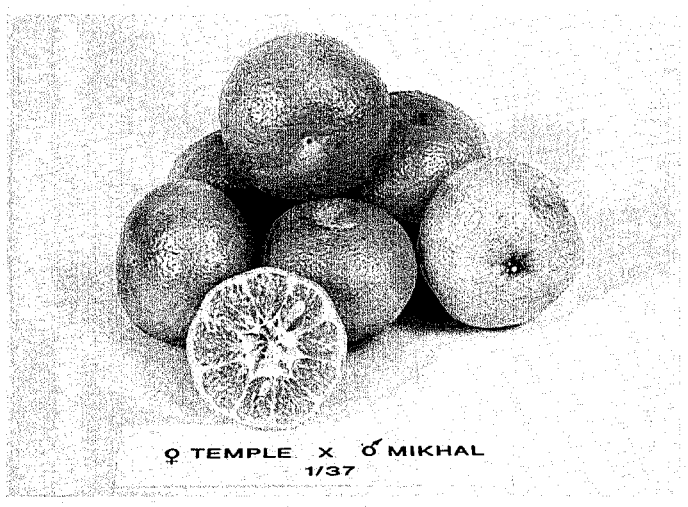
FIG. 1 shows whole fruit of the new variety illustrating the yellow-orange exterior of the fruit, as well as transverse midsections of the fruit in a plane substantially perpendicular to the axis of the fruit.

The following is a detailed description of the new mandarin citrus variety based on observations made under typical Israeli grove conditions.

Tree: The tree is medium sized, about 4 meters high by 4 meters wide at 5–6 years after planting. This is similar to Michal but larger than Temple which reaches only about 3 meters. The tree's vigor is also medium with an annual terminal growth after pruning of about 100–110 cm in length and 10–12 mm in diameter as measured in 1991 in Bet Dagan Israel which is similar to Michal but somewhat greater than Temple.

The chromosome number of the tree is diploid (2n=18) as is the chromosome number of Temple and Michal. The foliar canopy is quite dense. The color of the bark of the older parts of the tree is brown-gray. The branches of the tree are slightly willowy. The tree is self pollinating and quite productive with a tendency to alternate bearing. There is little propensity for the tree to produce water sprouts. The fruit bearing branches are almost thornless, but water shoots are thorny. The tree is basally dominant. Main branches have an upright attitude and young shoots have no anthocyanin coloration at the tip.

Leaf: Foliar flushes, as measured in Bet Dagan, Israel in 1991, occur between April and September. The color and veination of the leaves are similar to that of Michal and Temple. The leaves are somewhat variable, medium to small, lanceolate and sharp pointed. Leaf blades are firm, without undulation and straight in cross section. Petioles are without wings or have rudimentary wings.

Flower: Flowering, as measured in Bet Dagan, Israel, in 1991 occurs between mid March and the beginning of April. Terminal flower buds have no anthocyanin coloration. Flowers are borne singly and have an average number of stamens (about 20) with incomplete style development. Another color is yellow with viable pollen present and trees flower once per year.

Fruit ripening as measured in 1991 in Bet Dagan, Israel, is from the last week of September to mid-October for trees grafted on Troyer root stock and from mid-October to the beginning of November for trees grafted on Sour Orange rootstocks. This is advantageously early as compared with other cultivars such as Temple which ripens in late January to February and Michal which ripens in mid-November. The fruit ripens uniformly throughout the canopy, however, fruit on the outside of the canopy is somewhat lighter in color. In addition, the fruit color takes on a red blush at ripening. Thinning is not required.

The early abortion of set fruit (June drop) is similar to Temple and Michal. After ripening the fruits do not regreen if left on the tree, however, if the fruit is not harvested within one month of ripening it becomes more acidic and develops an off flavor.

The fruit is oblate to rounded, and small to medium sized with an a verage weight of 95 gms, a height of 45–55 mm and fruit diameter of 55–63 mm. The fruit has a short necked or evenly rounded basal end and a depressed distal end. The fruit surface is slightly wrinkled with a yellow orange color, 21B on The Royal Horticultural Society of London Colour Chart, and bears conspicuous, but sparsely distributed ring oil glands. The rind is thin and the flesh adheres weakly to the rind. A style does not persist and a navel is not present or very rare. An aerola is present and fully developed. The fruit stem is about 3 mm in diameter.

The above fruit characteristics differ from both Temple and Michal. Temple has a medium-large fruit, a very broadly oblate to slightly subglobose shape, sometimes with a shortwrinkled or furrowed neck and a medium thick moderately adherent but readily peelable rind with a deep reddish-orange color and a somewhat pebbled or rough surface. Michal has fruits of variable size ranging from small to medium, a slightly oblate to globose shape occasionally with a small naval and a smooth, easily peeled rind with a deep reddish-orange color.

The color of the albedo is white and the flesh is mainly orange in color. The columella is hollow and of large diameter. The fruit contains 9–11 segments and is very juicy.

The color of the juice is yellow-orange. The seeds are small, smooth and polyembryonic with few embryos as are the seeds of the pollen parent Michal. This is in contrast to the seeds of Temple which are monoembryonic. The external color of the seed is ivory both when fresh and when dry. Color of internal seed coat is brown and color of cotyledons is green. The fruit contains between 5 and 9 seeds, and the fruit is therefore characterized as having few seeds. Polyembryonic seeds are present and about 50% of the seeds are polyembryonic. The fruit reaches maturity early or very early in the season which is in late September or early October in Israel.

The results of a quality test conducted on the juice of representative ripe fruit of the novel variety Oct. 6, 1989 are as follows:

Total soluble solids (TSS): 11.0%.
Acid content: 1.4%.
TSS/acid ratio: 7.8.

The fruit flavor is very pleasant and similar to that of the pollen parent Michal.

I claim:

1. A novel variety of mandarin citrus substantially as herein shown and described, characterized by very early fruit ripening and fruit which is yellow-orange in color when fully ripe.

* * * * *